United States Patent [19]

Riva et al.

[11] Patent Number: 4,956,293
[45] Date of Patent: Sep. 11, 1990

[54] NOCARDIA SP. ATCC 53492, OR AN ANTIBIOTIC A 42867 PRODUCING MUTANT OR VARIANT THEREOF

[75] Inventors: Ernesto Riva; Maurizio Denaro, both of Milan; Enrico Selva, Gropello Cairoli; Giovanni Cassani, Pavia; Francesco Parenti, Lainate, all of Italy

[73] Assignee: Gruppo Lepetit S.p.A., Italy

[21] Appl. No.: 270,884

[22] Filed: Nov. 14, 1988

Related U.S. Application Data

[63] Continuation of Ser. No. 78,501, Jul. 28, 1987, Pat. No. 4,804,534.

[30] Foreign Application Priority Data

Jul. 29, 1986 [GB] United Kingdom ............... 8618445

[51] Int. Cl.$^5$ .................... C12N 1/20; C12R 1/365
[52] U.S. Cl. ............................ 435/253.2; 435/872
[58] Field of Search ........................ 435/253.2, 872

[56] References Cited

U.S. PATENT DOCUMENTS 2,990,329  6/1961  Philip et al. .................... 435/872
4,558,009 12/1985  Boeck et al. ................... 435/253.2

OTHER PUBLICATIONS

Dingerdissen, J. J. et al., "Actinoidin A$_2$, A Novel Glycopeptide: Production, Preparative HPLC Separation and Characterization", *J. of Antibiotics*, vol. 40(2), pp. 165–172, 1987.

Primary Examiner—Elizabeth C. Weimar
Assistant Examiner—Marian C. Knode
Attorney, Agent, or Firm—Dugal S. Sickert

[57] ABSTRACT

A novel antibiotic, A 42867, is prepared by cultivating the strain Nocardia sp. ATCC 53492, or an antibiotic A 42867-producing mutant or variant thereof, under submerged aerobic conditions in the presence of assimilable sources of carbon, nitrogen and inorganic salts. The antibiotic and its addition salts are useful in the treatment of infectious diseases and as growth promotant agents.

2 Claims, 3 Drawing Sheets

NOCARDIA SP. ATCC 53492, OR AN ANTIBIOTIC A 42867 PRODUCING MUTANT OR VARIANT THEREOF

This is a divisional, of application Ser. No. 078,501, filed July 28, 1987, now U.S. Pat No. 4,804,534.

The present invention is directed to a new antibiotic substance denominated antibiotic A 42867, the addition salts thereof, the pharmaceutical compositions thereof and their use as medicaments, particularly in the treatment of infectious diseases involving microorganisms susceptible to them.

The compounds of the invention are also active as growth promoting agents in animals, such as poultry, swine, ruminants, etc.

Another object of the invention is a process for preparing antibiotic A 42867 which includes culturing the new strain Nocardia sp. ATCC 53492 or an antibiotic A 42867-producing variant or mutant thereof.

Norcardia sp. ATCC 53492 has been isolated from a soil sample and was deposited on May 23, 1986 with the American Type Culture Collection (ATCC), 12301 Parklawn Drive, Rockville, 20852 Maryland, U.S.A. under the provisions of the Budapest Treaty. The strain has been accorded accession number ATCC 53492.

In view of their similar antimicrobial activities, reference to antibiotic A 42867 also includes reference to its pharmaceutically acceptable addition salt, and vice versa.

The production of antibiotic A 42867 is achieved by cultivating a Nocardia sp. capable of producing it, i.e. Nocardia sp. ATCC 53492 or an antibiotic A 42867-producing variant or mutant thereof, under aerobic conditions in an aqueous nutrient medium containing assimilable sources of carbon, nitrogen, and inorganic salts. Many of the nutrient media usually employed in the fermentation art can be used, however certain media are preferred. Preferred carbon sources are glucose, mannose, galactose, starch, corn meal and the like. Preferred nitrogen sources are ammonia, nitrates, soybean meal, peptone, meat extract, yeast extract, tryptone, aminoacids, and the like. Among the inorganic salts which can be incorporated in the culture media there are the customary soluble salts capable of yielding sodium, potassium, iron, zinc, cobalt, magnesium, calcium, ammonium, chloride, carbonate, sulfate, phosphate, nitrate and like ions.

Ordinarily, the antibiotic-producing strain is pre-cultured in a shake flask, then the culture is used to inoculate jar fermentors for production of substantial quantities of the antibiotic substances. The medium used for the pre-culture can be the same as that employed for larger fermentations, but other media can also be employed. The antibiotic A 42867 producing-strain can be grown at temperatures between 20° and 40° C., preferably between 24° and 35° C.

During fermentation, the antibiotic production can be monitored by testing broth or mycelial extract samples for antibiotic activity, for instance, by bioassays or TLC or HPLC procedures.

Sensitive organisms to antibiotic A 42867 such as *Bacillus subtilis* and *S. aureus* can be used as test organisms. The bioassay is conveniently performed by the agar diffusion method on agar plates. Maximum production of antibiotic activity generally occurs between the second and the fifth day of fermentation.

Antibiotic A 42867 is produced by cultivating the strain Nocardia sp. ATCC 53492, or an antibiotic A 42867 producing mutant or varient thereof, and is mainly found in the culture broths.

Figure 1:
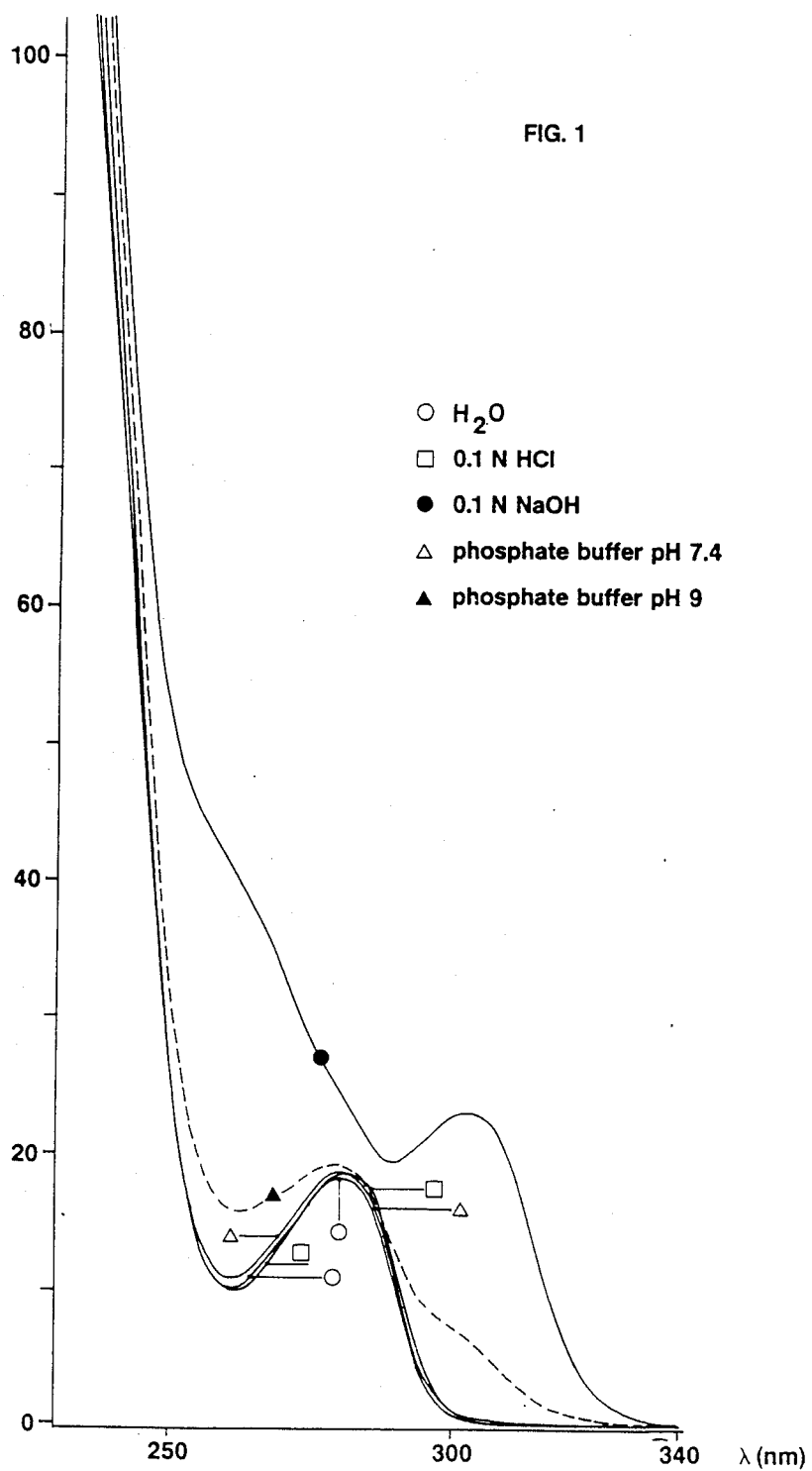
FIG. 1—Ultraviolet absorption spectrum of antibiotic A 428671.

Morphological properties of Nocardia sp. ATCC 53492

The morphology of this strain cultured on soil agar medium is similar to that one of actinomycetes showing a development of an abundant aerial mycelium with long hyphae moderately branched. A major morphological characteristic of this strain is the fragmentation of substrate and aerial mycelium in rodlike elements. Fragmentation of substrate mycelium was observed on all agar media used for the cultural characteristics but on medium No. 5, medium No. 7, Hickey-Tresner, and egg albumin a complete fragmentation was noted. Substrate hyphae of Nocardia sp. ATCC 53492 were fully developed with branched and fragmented rodlike elements depending on the age of the culture. Aerial mycelium was well developed on soil agar and on water agar. The aerial hyphae were long straight on soil agar forming sometimes knots or nest-like tangles. The morphology of this strain resembles the one of Nocardia genus.

The morphological characterization of this strain was accomplished on the same plates employed for studying the cultural properties. To establish if fragmentation occured on agar plates, the surface of the medium was taken out with a plastic knife and the specimen was observed on a glass slide under an optical microscope. In liquid culture this strain showed an extensive fragmentation into bacillary elements.

Cultural characteristics of Nocardia sp. ATCC 53492

For the examination of the cultural characteristics, Nocardia sp. ATCC 53492 was cultivated on various standard media suggested by Shirling and Gottlieb (Shirling E. B. and Gottlieb D., 1966—Method for characterization of Streptomyces species—Int. J. Syst. Bacteriol, 16, 313–340) with the addition of several media recommended by Waksman (Waksman, S. A. 1961—The Actinomycetes—The Williams and Wilkins Co. Baltimore; Vol. 2, 328–334).

Color determination was made when necessary by the method of Maerz and Paul (Maerz A. and M. Rea Paul, 1950—A Dictionary of Color—2nd Edition McGraw-Hill Book Company Inc. New York).

The ability of the organism to utilize different carbon sources was investigated by the method described by Shirling and Gottlieb.

The cultural and physiological characteristics and the carbon sources utilization are reported in Tables I, II, III, IV and V.

The readings in Table I have been taken after two week incubation at 28° C.

TABLE I

CULTURAL CHARACTERISTICS OF STRAIN
Nocardia sp. ATCC 53492

| Culture media | Characteristics |
|---|---|
| Medium No. 2 (yeast extract | Abundant growth, surface wrinkled, color brown |

TABLE I-continued
CULTURAL CHARACTERISTICS OF STRAIN
*Nocardia sp.* ATCC 53492

| Culture media | Characteristics |
| --- | --- |
| -malt agar) | 15/H/11, soluble pigment yellow |
| Medium No. 3 (oatmeal agar) | Moderate growth, surface smooth, color orange 12/L/12, trace aerial mycelium white |
| Medium No. 4 (inorganic salts-starch agar) | Abundant growth, surface wrinkled, color orange-dark 13/L/12, trace aerial mycelium white, trace of soluble pigment color rose |
| Medium No. 5 (glycerol-asparagine agar) | Abundant growth, surface wrinkled, color orange-dark 13/L/12, trace aerial mycelium white |
| Medium No. 6 (peptone-yeast extract iron agar) | Moderate growth, surface slightly wrinkled, color apricot 10/F/7 |
| Medium No. 7 (tyrosine agar) | Abundant growth, surface wrinkled, color brown 15/H/11, trace aerial mycelium white |
| Czapek-sucrose agar | Abundant growth, surface smooth, color yellow-orange 9/G/8, trace aerial mycelium |
| Oatmeal agar | Abundant growth, surface slightly wrinkled, color orange 12/F/10, trace aerial mycelium white, trace of soluble pigment rose |
| Hickey and Tresner's agar | Abundant growth, surface wrinkled, color golden 9/I/6 |
| Calcium malate agar | Abundant growth, surface smooth, color pale yellow 10/C/4, trace aerial mycelium white |
| Bennett's agar | Abundant growth, surface wrinkled, color brown 15/H/11 |
| Czapek glucose agar | Abundant growth, surface wrinkled, color brown 7/E/12, trace aerial mycelium white, soluble pigment dark yellow |
| Glucose asparagine agar | Moderate growth, surface slightly crusty, color yellow 10/L/5 |
| Nutrient agar | Abundant growth, surface smooth, color yellow-orange 9/G/6/ |
| Skim milk agar | Abundant growth, surface smooth, color peach 9/I/5, trace aerial mycelium white |
| Egg albumin agar | Moderate growth, surface smooth, colorless, trace aerial mycelium |
| Sabouraud agar | Abundant growth, surface wrinkled, color brown 10/L/10 |
| Potato agar | Abundant growth, surface wrinkled, color yellow 10/L/7, trace aerial mycelium white soluble pigment rose |
| Water agar | Very scant growth, surface smooth, colorless, good formation of aerial mycelium white |
| Soil agar | Moderate growth, surface smooth, colorless, abundant formation of aerial mycelium |
| Dextrose tryptone agar | Abundant growth, surface wrinkled, color yellow 10/L/7 |

Letters and numbers refer to the color determined according to Maerz and Paul (2)

Physiological characteristics of Nocardia sp. ATCC 53492

TABLE II

| Tests | Results |
| --- | --- |
| Starch hydrolysis | positive |
| Tyrosine reaction | positive |
| Casein hydrolysis | positive |
| Solubilization of calcium malate | negative |
| Nitrite from nitrate | negative |
| Cellulose decomposition | negative |
| Production of hydrogen sulfide | positive with lead acetate strips |
| Litmus milk { peptonization | positive |
| Litmus milk { coagulation | negative |

Temperature tolerance

TABLE III

| | |
| --- | --- |
| 15° C. = | − |
| 22° C. = | + |
| 28° C. = | ++ |
| 37° C. = | ++ |
| 42° C. = | + |
| 50° C. = | − |

The most suitable temperature for the development of the colonies was found to range from about 22° C. to about 42° C.

The optimum temperature is from 28° C. to 37° C.

pH tolerance

TABLE IV

| | |
| --- | --- |
| pH 3 = | − |
| pH 4 = | − |
| pH 5 = | ++ |
| pH 6 = | ++ |
| pH 7 = | ++ |
| pH 8 = | ++ |
| pH 9 = | ++ |
| pH 10 = | − |
| pH 11 = | − |

− = No growth
+ = Moderate growth
++ = Abundant growth

For physiological characteristics, pH and temperature tolerance experiments Hickey and Tresner's agar medium was employed.

Utilization of carbon sources

TABLE V

| Carbon utilization | |
| --- | --- |
| Carbon Source | Growth |
| Lactose | ++ |
| Arabinose | ++ |
| Xylose | ++ |
| Mannose | ++ |
| Fructose | ++ |
| Cellobiose | ++ |
| Galactose | ++ |
| Inositol | ++ |
| Glucose | ++ |
| Raffinose | − |

TABLE V-continued

| Carbon Source | Carbon utilization Growth |
|---|---|
| Ribose | + + |
| Sucrose | − |
| Salicin | + |
| Cellulose | − |
| Rhamnose | − |

− = no growth
+ = moderate growth
+ + = abundant growth

For this test medium No. 8 was employed and the results taken after 10 days of incubation at 28° C.–30° C.

Chemotaxonomical studies

The strain was cultured in V-6 medium (beef extract 0.5%, autolyzed yeast 0.5%, peptone 0.5%, hydrolized casein 0.3%; glucose 2%, NaCl 0.15%), incubated on a rotary shaker at 200 rpm at 30° C. for 72 hours. The mycelium grown in V-6 medium was harvested by centrifugation (3000 rpm×10 minutes), and washed twice with distilled water. The mycelium was further washed with ethanol, followed by drying at room temperature under a laminar flow.

The dried mycelium was used as a whole-cell preparation.

Amino acids analysis:

The amino acids analysis carried out as described by Becker et al., ("Rapid differentiation between Nocardia and Streptomyces by paper chromatography of whole cell hydrolysates", Appl. Microbiol. 12, 421–423 (1964)) showed the presence of meso-diaminopimelic acids.

Sugar analysis:

Analysis of sugar content carried out according to M. P. Lechevalier, ("Identification of aerobic actinomycetes of clinical importance", J. Lab. Clin. Med. 71, 934–944 (1968)), using thin layer chromatography sheets as described by J. L. Staneck and G. D. Roberts, ("Simplified approach to identification of aerobic actinomycetes by thin-layer chromatography", Appl. Microbiol., 28, 226–231 (1974), showed the presence of arabinose and galactose.

Identity of Nocardia sp. ATCC 53492

The presence of meso-diaminopimelic acids together with diagnostic sugars such as galactose and arabinose indicates that this strain is an actinomycetes with cell wall type IV, according to the classification of Lechevalier M. P., and H. Lechevalier, ("Chemical composition as a criterion in the classification of aerobic actinomycetes", Int. Journ. Syst. Bacteriol. 20, 435–443 (1970)).

As with other microorganisms, the characteristics of the A 42867 producing strain are subject to variation. For example, artificial variants and mutants of the strain can be obtained by treatment with various known mutagens, such as U.V. rays, X-rays, high frequency waves, radioactive rays, and chemicals such as nitrous acid, N-methyl-N'-nitro-N-nitrosoguanidine, and many others. All natural and artificial variants and mutants which belong to the species of the genus Nocardia and produce A 42867 antibiotics, are deemed equivalent to strain Nocardia sp. ATCC 53492 and are contemplated to be within the scope of this invention.

The recovery of A 42867 antibiotics from the fermentation broths of the producing microorganism is conducted according to known per se techniques which include extraction with solvents, precipitation by adding non-solvents or by changing the pH of the solution, partition chromatography, reverse-phase partition chromatography, ion-exchange chromatography, affinity chromatography and the like.

A preferred procedure includes an affinity chromatography on immobilized D-Alanyl-D-Alanine followed by reverse-phase column chromatography.

Immobilized D-Alanyl-D-Alanine matrices suitable for the present recovery process are disclosed in European Patent Application No. 83112555. The preferred matrix in the present process is D-Alanyl-D-alanine coupled with a controlled pore cross-linked polydextrane.

The filtered fermentation broths are then subjected to an affinity chromatography on immobilized D-Alanyl-D-Alanine, either in column or batchwise.

The binding of the A 42867 antibiotic substance to the affinity matrix is preferably made at a pH of about 7.0–8.0 and its elution is performed at more basic pH values (preferably between 9.0 and 11.5) by means of an aqueous base. This aqueous base may be ammonia, a volatile amine, an alkali or alkali metal hydroxide or a basic buffered solution optionally in the presence of a polar organic solvent such as a polar water-miscible solvent as defined below.

After removing the impurities by rinsing the column with aqueous buffer pH 4–8, optionally containing salts, urea and/or water miscible solvents, antibiotic A 42867 is eluted with the above described eluting mixture. The crude antibiotic substance is then recovered preferably by removing water completely from the pooled antibiotic-containing fractions by azeotropical distillation with an organic solvent capable of forming minimum azeotropic mixtures with water, followed by addition of a non-solvent to precipitate the desired product.

Representative examples of organic solvents capable of forming minimum azeotropic mixtures with water are n-butanol, benzene, toluene, butyl ether, carbon tetrachloride, chloroform, cyclohexane, 2,5-dimethylfurane, hexane and m-xilene; the preferred solvent being n-butanol.

Examples of non-solvents are: petroleum ether, lower alkyl ethers, such as ethyl ether, propyl ether and butyl ether, and lower alkyl ketones such as acetone.

Alternatively, the pooled antibiotic-containing fractions are concentrated to a small volume, preferably by azeotropical distillation with an organic solvent defined as above, and the resulting aqueous solution is lyophilized.

If the aqueous base employed in the elution is nonvolatile, it may be necessary to neutralize and desalt the concentrate before precipitation or freeze-drying.

A convenient desalting procedure includes applying the antibiotic containing aqueous solution to a silanized silica gel column, washing with distilled water and eluting with a mixture of a polar water-miscible solvent and water.

Representative examples of polar water-miscible solvents are: water-soluble alcohols, (such as methanol, ethanol, iso-propanol, n-butanol), acetone, acetonitrile, lower alkyl alkanoates (such as ethyl acetate), tetrahydrofuran, dioxane and dimethylformamide and mixtures thereof; the preferred polar water-miscible solvent being acetonitrile.

Alternatively, desalting may be carried out by applying the antibiotic containing solution to the above described affinity column, washing with distilled water and eluting with a volatile aqueous base as described above for the elution of the affinity chromatography.

The product so obtained is antibiotic A 42867. A convenient procedure to obtain pure antibiotic A 42867 is represented by a further purification as obtained above on an affinity chromatography column. The same stationary phase as above (immobilized D-Alanyl-D-Alanine) is generally used and the desired antibiotic substance is eluted by following the affinity chromatography procedure on immobilized D-Alanyl-D-Alanine described above.

A preferred immobilized D-Alanyl-D-Alanine is Sepharose-$\epsilon$-aminocaproyl-D-Alanyl-D-Alanine, a preferred equilibrating mixture is 0.16% (w/v) ammonia containing 2M NaCl adjusted to pH 7–8, a preferred rinsing solution is 0.16% (w/v) ammonia containing 2M NaCl adjusted to pH 7–8, a preferred eluting mixture is 0.16% (w/v) ammonia.

Alternatively, the antibiotic substance of the invention may be isolated from the fermentation broth or further purified by means of strong or weak anion resins including functionalized polystyrene, acrylic or polydextrane matrices. Examples of weak anion exchange resins are those sold under the following trade-names: Dowex MWA-1 or WGR (Dow Chemical), Amberlite IRA-73 (Rohm and Haas), DEAE-Sephadex (Pharmacia). Examples of strong anion exchange resins which may be used according to invention include those sold under the following trade names: Dowex MSA-1, SBR, SBR-P (Dow Chemical), Amberlite IR-904 (Rohm and Haas) and QAE-Sephadex (Pharmacia).

The elution of the A 42867 antibiotic substance from these resins is conducted by means of linear gradient mixtures of aqueous solution of electrolytes, such as sodium or potassium hydrochlorides, in water or mixtures of water and an organic water-miscible solvent such as a lower alcohol (e. g. ($C_1$-$C_4$)alkanol) or lower alkyl ketones (e.g. acetone, methylethyl ketone, etc.)

Physico-chemical characteristics of antibiotic A 42867

(A) ultraviolet absorption spectrum, which is shown in FIG. 1 of the accompanying drawings, and exhibits the following absorption maxima:

|     |                        | λ max (nm)        |
| --- | ---------------------- | ----------------- |
| (a) | 0.1 N HCl              | 282               |
| (b) | Water                  | 282               |
| (c) | phosphate buffer pH 7.4| 282               |
| (d) | phosphate buffer pH 9  | 282               |
|     |                        | 305 (shoulder)    |
| (e) | phosphate buffer 0.1 KOH | 305             |
|     |                        | 265 (shoulder)    |

Figure 2:
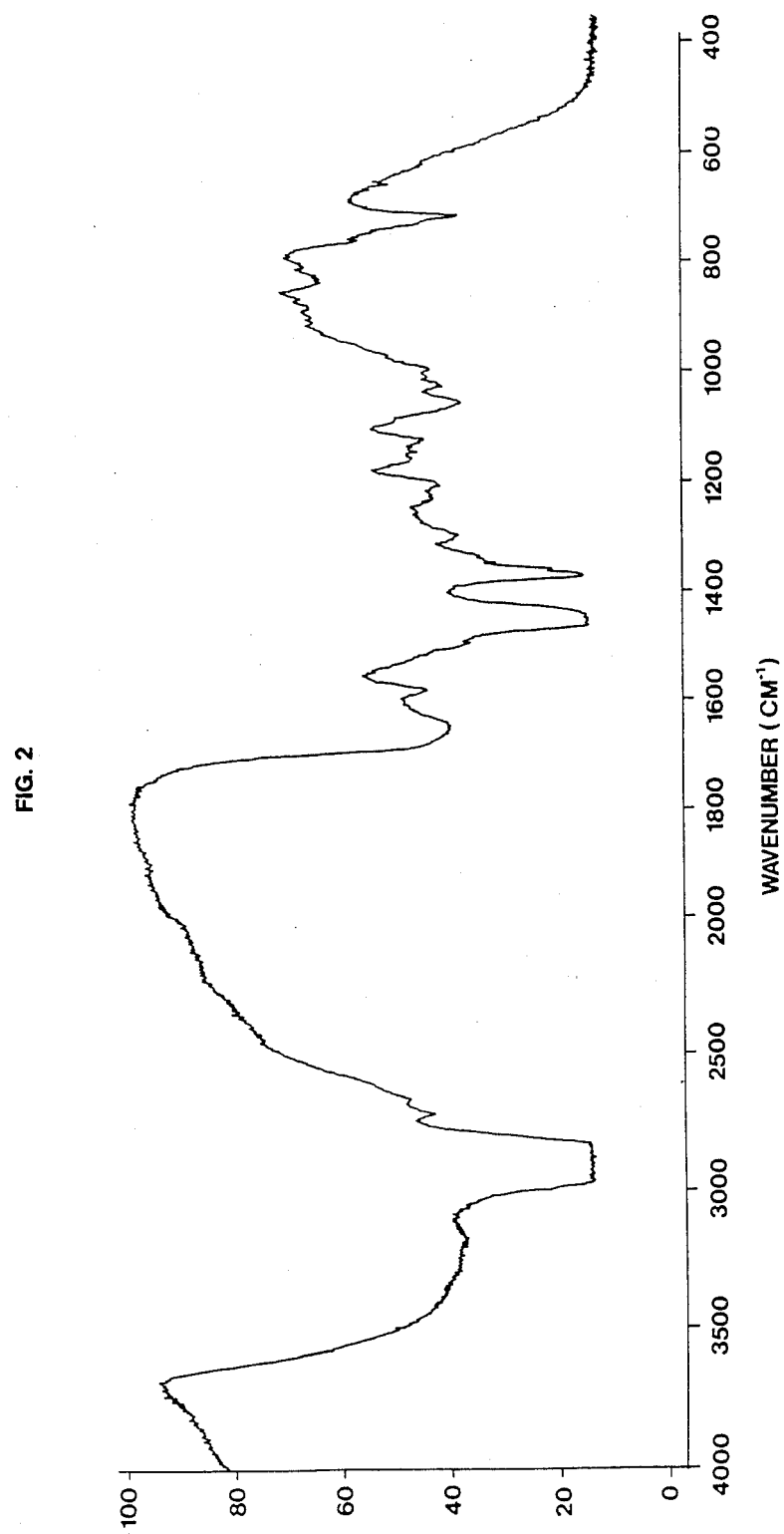
FIG. 2—Infrared absorption spectrum of antibiotic A 42867.

(B) infrared absorption spectrum which is shown in FIG. 2 of the accompanying drawings and exhibits the following absorption maxima (cm$^{-1}$): 3700–3100, 3000–2800 (nujol); 1650; 1580; 1460 (nujol) 1375 (nujol); 1300; 1235; 1210; 1160; 1130; 1060; 1025; 1000; 970; 840; 790–700; 720 (nujol)

Figure 3:
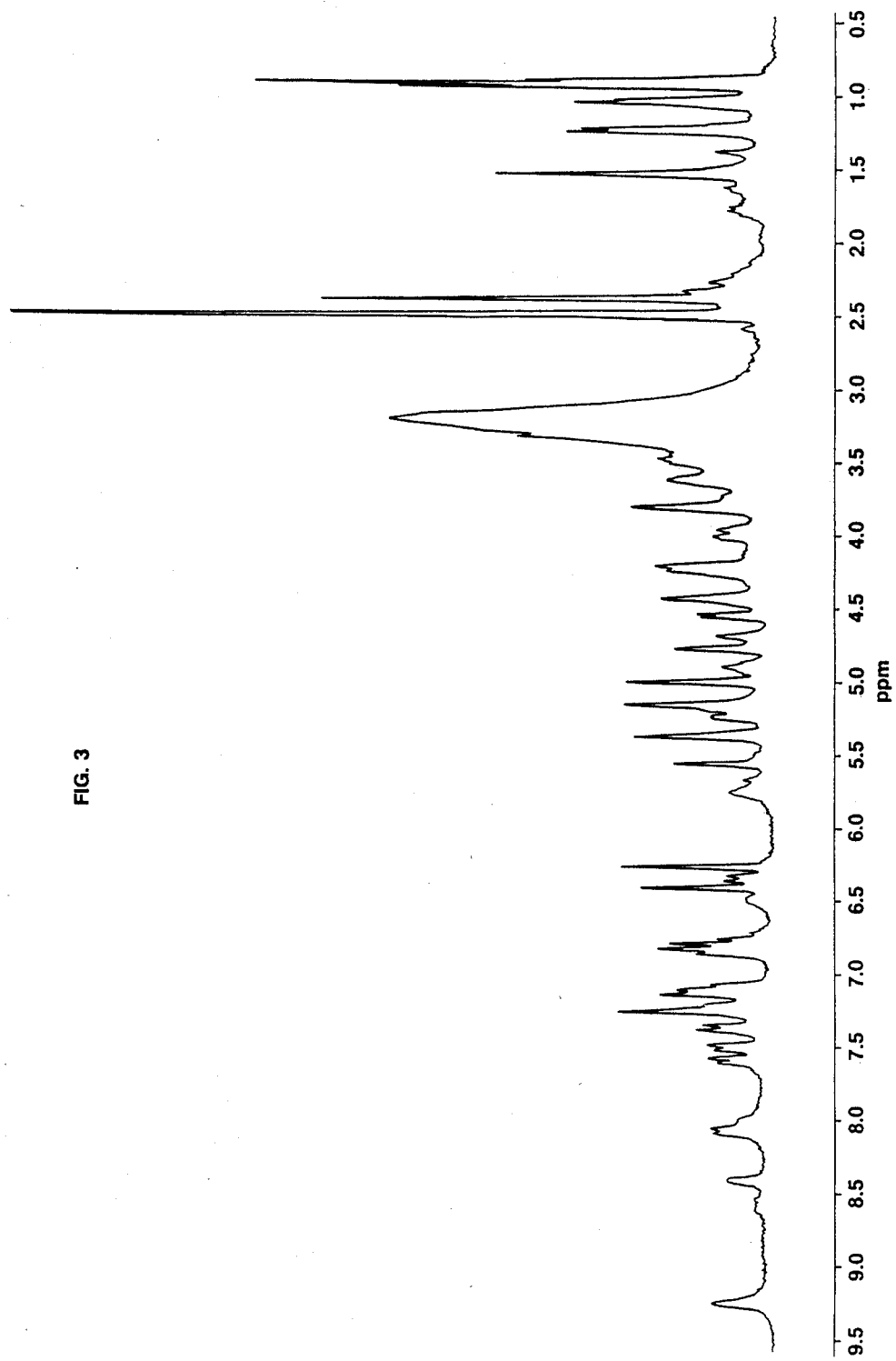
FIG. 3—¹H-NMR spectrum of antibiotic A 42867.

(C) $^1$H-NMR spectrum which is shown in FIG. 3 and exhibits the following groups of signals (in ppm) at 270 MHz recorded in DMSO $d_6$ (hexadeuterodimethylsulfoxide) using TMS as the internal standard (0.00 ppm), ($\delta$=ppm): 0.90, d [($CH_3$)$_2$—(CH)]; 1.02, d [$CH_3$—(CH)]; 1.23, d [$CH_3$—(CH)]; 1.52, s [$CH_3$—C]; 1.77, m [CH($CH_3$)$_2$]; 2.38, s (N—$CH_3$); 3.0–6.35, s and m (aromatic, sugar and peptidic CH's); 6.27–9.29 (aromatic CH's, peptidic NH's and phenolic OH's)

d=doublet
s=singlet
m=multiplet (D) retention-time ($R_t$) of 0.537 relative to Vancomycin.HCl (Vancocin, Eli Lilly, $R_t$=16.36 min) when analyzed by reverse phase HPLC under the following conditions:
column: Ultrasphere ODS (5 $\mu$m) Altex (Beckman) 4.6 mm (i.d.)$\times$250 mm
pre-column: Brownlee Labs RP 18 (5 $\mu$m)
eluent: Water:acetonitrile:2-ethanolamine:trifluoroacetic acid 9:1:0.01:0.01 (v/v)
flow rate: 1.6 ml/min
U.V. detector: 254 nm
internal standard: Vancomycin.HCl ($R_t$=16.36 min) (Vancocin, Eli Lilly)

(E) retention-time ($R_t$) of 0.665 relative to Vancomycin.HCl (Vancocin, Eli Lilly, $R_t$ 9.96 min) when analyzed by reverse phase HPLC under the following conditions:
column: Ultrasphere ODS (5 $\mu$m) Altex (Beckman) 4.6 mm (i.d.)$\times$250 mm
pre-column: Brownlee Labs RP 18 (5 $\mu$m)

| eluent A: | $CH_3CN$ | 2% | adjusted at pH 6.0 |
|---|---|---|---|
|  | (2.5 g/l) $NaH_2PO_4.H_2O$ | 98% | |
| eluent B: | $CH_3CN$ | 70% | adjusted at pH 6.0 |
|  | (2.5 g/l) $NaH_2PO_4.H_2O$ | 30% | | elution: linear gradient from 5% to 60% of eluent B in eluent A, in 40 min
flow rate: 1.6 ml/min
U.V. detector: 254 nm
internal standard: Vancomycin.HCl ($R_t$=9.96 min) (Vancocin, Eli Lilly)

(E) elemental analysis, after the sample has been previously dried at about 140° C. under inert atmosphere which indicates the following approximate percentage composition (average): carbon 53.3%; hydrogen 5.9%; nitrogen 7.85%; chlorine (total) 4.41%; chlorine (ionic) 2.22%. Inorganic residue at 900° C. in the air: 0.875%.

(G) acid-base titration profile in water upon titration with 0.05N aqueous KOH of a sample previously added with excess of aqueous HCl which shows pKa values at 3.2, 7.1 and 8.3

(H) $R_f$ value of 0.56 in the following chromatographic system:

| (Aqueous sodium chloride) 87.5 g/l:$NaH_2PO_4$ 0.5 g/l | 70% | adjusted to pH 6 |
|---|---|---|
| $CH_3CN$ | 30% | | using reverse-phase silanized silica gel plates (RA-18 $F_{254}$)
Visualization:
U V. light at 254 nm
Yellow color with Pauly Reagent, i.e. diazotized sulfanilic acid (J. Chromatog. 20, 171 (1965), Z. Physiol. Chem. 292, 99, (1953))
Bioautography using B. subtilis ATCC 6633 on minimal Davis medium.

(I) MW of about 1559 desumed from a FAB-MS spectrum showing the M+H⊕ peak at 1560

Antibiotic A 42867 possesses acid and basic functions and besides forming internal salts under proper pH conditions can form salts with organic and inorganic counter-ions according to conventional procedures.

Representative and suitable acid addition salts of the compounds of the invention include those salts formed by the standard reaction with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, pamitic, cholic, pamoic, mucic, glutamic, camphoric,glutaric, glycolic, phthalic, tartaric, lauric,- stearic, salicylic, methanesulfonic, benzenesulfonic, sorbic, picric, benzoic, cinnamic and the like acids.

Representative examples of these bases are: alkali metal or alkaline-earth metal hydroxide such sodium, potassium, calcium, magnesium, barium hydroxide; ammonia and aliphatic, alicyclic or aromatic organic amines such as methylamine, dimethylamine, trimethylamine, and picoline.

The transformation of the "non-salt" compounds of the invention into the corresponding addition salts, and the reverse, i.e. the transformation of an addition salt of a compound of the invention into the non-salt form, are within the ordinary technical skill and are encompassed by the present invention.

For instance antibiotic A 42867 can be transformed into the corresponding acid addition-salt by dissolving the non-salt form in an aqueous solvent and adding a slight molar excess of the selected acid or base. The resulting solution or suspension is then lyophilized to recover the desired salt.

In case the final salt is unsoluble in a solvent where the non-salt form is soluble it is recovered by filtration from the organic solution of the non-salt form after addition of the stoichometric amount or a slight molar excess of the selected acid or base.

The non-salt form can be prepared from a corresponding acid or base salt dissolved in an aqueous solvent which is then neutralized to free the non-salt form.

When following the neutralization the elimination of the excess of acid or base is necessary, a common desalting procedure may be employed.

For example, column chromatography on silanized silica gel, non-functionalized polystyrene, acrylic and controlled pore polydextrane resins (such as Sephadex LH 20) or activated carbon may be conveniently used. After eluting the undesired salts with an aqueous solution, the desired product is eluted by means of a linear gradient or a step-gradient of a mixture of water and a polar or apolar organic solvent, such as acetonitrile/water from 50:50 to about 100% acetonitrile.

As it is known in the art, the salt formation either with pharmaceutically acceptable acids (or bases) or non-pharmaceutically acceptable acids (or bases) may be used as a convenient purification technique. After formation and isolation, the salt form of an A 42867 antibiotic can be transformed into the corresponding non-salt form or into a pharmaceutically acceptable salt form.

In some instances, a base addition salt of antibiotic A 42867 is more soluble in water and hydrophilic solvents. The antibacterial activity of the compound of the invention can be demonstrated in vitro by means of standard dilution tests on different microorganism cultures.

Culture media and growth conditions for MIC (minimal inhibitory concentration) determinations were as follows: Isosensitest broth (Oxoid), 24 h, for staphylococci, Strep. faecalis, and Gram-negative bacteria (Escherichia coli); Todd-Hewitt broth (Difco), 24 h for other streptococcal species; GC base broth (Difco)+1% Isovitalex (BBL), 48 h, $CO_2$-enriched atmosphere for Neisseria gonorrhoeae; Brain Heart broth (Difco)+1% Supplement C (Difco), 48 h for Haemophilus influenzae; AC broth (Difco), 24 h, anaerobic atmosphere for Clostridium perfringens; Wilkins-Chalgren agar (ref: T. D. Wilkins & S. Chalgren, 1976, Antimicrob. Agents Chemother. 10, 926), 48 h, anaerobic atmosphere for the other anaerobes (C. difficile, Propionibacterium acnes, Bacteroides fragilis); PPLO broth (Difco)+10% horse serum+1% glucose, 48 h for Mycoplasma gallisepticum; PPLO broth with supplements as in R. T. Evans and D. Taylor-Robinson J. Antimicrob. Chemother. 4, 57, 24 h for U. urealyticum. Incubation was at 37° C. Inocula were as follows: 1% (v/v) of a 48 h broth culture for M. gallisepticum; about $10^4$ color-changing units/ml for U. urealyticum; about $10^4$–$10^5$ colony-forming units/ml for other broth dilution MICs; about $10^4$–$10^5$ bacteria/spot (inoculated with a multipoint inoculator) for agar dilution MICs (C. difficile, P. acnes, B. fragilis).

The minimal inhibitory concentrations (MIC, μg/ml) for some microorganisms are reported below in Table I.

TABLE VI

| Strain | M.I.C. (μg/ml) Antibiotic A 42867 |
|---|---|
| Staph. aureus L165 ($10^4$ cfu/ml) | 0.25 |
| Staph. epidermidis L147 ATCC 12228 (coagulase negative | 1 |
| Strep. pyogenes L49 C203 | 0.13 |
| Strep. pneumoniae L44 UC41 | 0.13 |
| Strep. faecalis L149 ATCC 7080 | 1 |
| Strep. mitis L796 (clinical isolate) | 0.25 |
| Clostridium perfringens L290 ISS 30543 | 0.13 |
| Clostridium difficile L1363 ATCC 9689 | 2 |
| Propionibacterium acnes L1014 ATCC 6919 | 0.5 |
| Neisseria gonorrhoeae L997 ISM56/126 | >128 |
| Haemophilus influenzae type b L 970 ATCC 19418 | >128 |
| Proteus vulgaris ATCC 881 L 79 | >128 |
| Escherichia coli L47 SKF 12140 | >128 |
| P. aeruginosa ATCC 10145 L 4 | >128 |
| Candida albicans SKF 2270 L 145 | >128 |
| Mycoplasma gallisepticum L431 S6 Weybridge | >128 |

Antibiotic A 42867 has been found active against coagulase negative staphylococci. The M.I.C. (μg/ml) relative to a series of clinical isolates of S. epidermidis and S. haemolyticus are reported below:

TABLE VII

| Strain | Antibiotic A 42867 M.I.C. (μg/ml) |
|---|---|
| S. epidermidis L 393 | 1 |
| S. epidermidis L 408 | 1 |
| S. epidermidis L 410 | 0.5 |
| S. haemolyticus L 381 | 4 |
| S. haemolyticus L 382 | 8 |
| S. haemolyticus L 383 | 1 |

The antimicrobial activity of the compounds of the invention is confirmed also in experimental septicemia in the mouse.

Control and treatment groups contained ten CD-1 mice (Charles River) weighing 18–22 g. They are infected intraperitoneally with 0.5 ml of bacterial suspension prepared by diluting an overnight culture of S. pyogenes C 203 (L 49) with sterile peptonized saline. Inocula were adjusted so that untreated animals died of septicemia within 48 h. The compounds to be tested were administered subcutaneously immediately after infection. On the 7th day, the $ED_{50}$ in mg/kg was calculated by the method of Spearman and Kärber (D. J. Finney "Statistical Methods in Biological Assay", Griffin, page 524, 1952) from the percentage of surviving animals at each dose.

Under these conditions the $ED_{50}$ value of antibiotic A 42867 was 1.54 mg/kg.

In general, for antibacterial treatment antibiotic A 42867 as well as the non-toxic pharmaceutically acceptable salts thereof or mixture thereof, can be administered by different routes such as topically or parenterally. The parenteral administration is, in general, the preferred route of administration.

Compositions for injection may take such forms as suspensions, solutions, or emulsions in oily or aqueous vehicles, and may contain adjuvants such as suspending, stabilizing and/or dispersing agents.

Alternatively, the active ingredient may be in powder form for reconstitution at the time of delivery when a suitable vehicle, such as sterile water, is added thereto.

Depending on the route of administration, these compounds can be formulated into various dosage forms.

In some instances, it may be possible to formulate the compounds of the invention in enteric-coated dosage forms for oral administration which may be prepared as known in the art (see for instance "Remington's Pharmaceutical Sciences", fifteenth edition, Mack Publishing Company, Easton, Pa., U.S.A., page 1614).

This could be especially the case when the absorption of the antimicrobial substance in the enteric tract is particularly desired while passing unaltered through the gastric tract.

The amount of active principle to be administered depends on various factors such as the size and condition of the subject to be treated, the route and frequency of administration, and the causative agent involved.

The antibiotic substances of the present invention and the physiologically acceptable salts thereof, are generally effective at a daily dosage of between about 0.5 and 50 mg of active ingredient per kilogram of patient body weight, optionally divided into 1 to 4 administrations per day.

Particularly desirable compositions are those prepared in dosage units containing from about 100 to about 5,000 mg per unit.

Representative examples of vehicles suitable for injection are: sterile water for injection, Ringer's solution, 0.9% saline and 5% dextrose. For i.v. infusion, the suitable concentration of the antibiotic in the vehicle is between about 5% and 10%. Other suitable formulations for dosage units are hermetically sealed vials, plastic pouches, sterile, rubber-stoppered vials and the like.

In addition, the antibiotic substance of the invention can be formulated in a topical preparation such as a solution, a cream or a lotion. These preparations conveniently contains from 0.1 to 15% (w/v) of the active ingredient.

Furthermore, the antibiotic substances of the invention are useful for suppressing the growth of *Clostridium difficile* which causes pseudomembranous colitis in the intestine. These antibiotics could be used in the treatment of pseudomembranous colitis by the oral administration of an effective dose of the antibiotics or a pharmaceutically-acceptable salt thereof, prepared in a pharmaceutically-acceptable dosage form. For such use, the antibiotics can be administered in gelatin capsules or in liquid suspension.

Besides its activity as medicament, antibiotic A 42867, or an acceptable salt thereof, can be used as an animal growth promoter.

For this purpose, a compound of the invention is administered orally in a suitable feed. The exact concentration employed is that which is required to provide for the active agent in a growth promotant effective amount when normal amounts of feed are consumed.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed.

The way in which such feed premixes and complete rations can be prepared and administered are described in reference books (such as "Applied Animal Nutrition", W. H. Freedman and CO., San Francisco, U.S.A., 1969 or "Livestock Feeds and Feeding", O and B books, Corvallis, Oreg., U.S.A., 1977) and are incorporated herein by reference.

The following examples further illustrate the invention and should not be interpreted as limiting it in any way.

EXAMPLE 1

Production of antibiotic A 42867

The stock culture of the producing organism (Nocardia sp. ATCC 53492) is streaked on oatmeal agar slants and incubated at 28° C. for 2 weeks. One loopful of strain growth is inoculated into a 500 ml Erlenmayer flask containing 100 ml of a seed medium composed of dextrose 2.0%, soybean meal 0.8%, yeast extract 0.2%, NaCl 0.1% and $CaCO_3$ 0.4% whose pH of the medium has been adjusted to 7.3 before sterilization. The flask is incubated on a rotary shaker at 28° C. for 72 hours. A 100 ml aliquot of the culture is then inoculated into a jar-fermentor containing 4 liters of the same seed medium and the culture is incubated at 28° C. for 48 hours with agitation of about 900 rpm and aeration of one standard liter of air per volume per minute. After inoculation of 4 liters of the seed culture into a jar fermentor containing 200 liter of fermentation medium having the same composition as the seed medium, fermentation is carried out for 96 hours with agitation of about 250 rpm and aeration of one standard liter of air per volume per minute.

The antibiotic activity was monitored by microbiological assay using *B. subtilis* cultured on minimal Davis medium.

EXAMPLE 2

Recovery of antibiotic A 42867

The whole fermentation broth (400 liters) obtained as described in Example 1 is filtered using a filter aid (Hyflo-FloMa ®), on a rotatory filter. The filtered broth is adjusted to pH 7.5 with 2 N hydrochloric acid, and added to 1000 ml of pre-swollen D-Ala-D-Ala-aminocaproyl-Sepharose-4B modified matrix (prepared as described in European Patent Application No. 83112555.4) and left overnight under slight stirring. The resin is recovered by filtration and washed with about 10 l of 0.5% (w/v) HCl-Tris buffer pH 7.5 which contains 5% (w/v)NaCl and then with water (4×5 l) while the broth is discharged.

The product selectively bound to the resin is eluted with 1.5% (w/v) ammonia hydroxide (4×5 l) and concentrated to a small volume (about 1800 ml) by means of azeotropical distillation with n-butanol under reduced pressure.

The concentrated aqueous solution is lyophilized obtaining crude antibiotic A 42867 (75.6 g).

EXAMPLE 3

Purification of crude antibiotic A 42867

Crude antibiotic A 42867 obtained by following the procedure of Example 2 (75 g) is dissolved in 2 liters of water containing 2 M sodium chloride, adjusted to pH 7.5 with 0.1 N sodium hydroxide solution, and then filtered.

The filtrate is applied at 500 ml/hour to a 1000 ml column (0.1×0.1 m) of pre-swollen D-Ala-D-Ala-6-amino-caproyl-Sepharose-4B modified matrix (prepared as described in European Patent Application No. 83112555.4) previously equilibrated with 0.04 M borate buffer pH 7.5 containing 2 M sodium chloride and 0.6 ml of Triton×100 (Baker grade).

The column is washed with 8 l of 8 M urea (pH 7.5) with flow rate of 500 ml/h followed by 70 l of aqueous NaOH at pH 10 collecting fractions of 1000 ml each. These fractions are assayed on B. subtilis cultures by agar-disc assay and those fractions which are inactive are discharged while those active (like fractions 63–70, in this case) are combined, concentrated to a small volume (500 ml) under reduced pressure by means of azeotropical distillation with n-butanol and lyophilized to give antibiotic A 42867 (4 g).

EXAMPLE 4

Purification and desalination of antibiotic A 42867

3.5 g of antibiotic A 42867 obtained by following the procedure of Example 3 is dissolved in 70 ml of a solution of sodium dihydrogen phosphate monohydrate (2.5 g/l) and acetonitrile (91:9) and filtered. 10 ml of this filtrate is applied to a stainless steel column (2×50 cm) packed with 40 g of 10 μm RP 18 Lichrosorb reverse-phase silica gel (Merck). The column is part of a Chromatospac Modulprep unit (Jobin Yvon, 16–18 Rue de Canal 91169 Longjumeau, France).

The column is eluted at 8 ml/min with the same solution used to dissolved the sample and fractions of 50 ml are collected.

Each fraction is monitored by HPLC and paper-disc bioassay on susceptible microorganisms such as B. subtilis.

The fractions active on B. subtilis of seven runs are combined, acetonitrile is removed by distillation under reduced pressure and the residue is diluted with a quantity of water which was about the volume of the initial solution.

The solution is adjusted to pH 7.5 and later applied a flow rate of 100 ml/h to a column (5×15 cm) of pre-swollen D-Ala-D-Ala-6-aminocaproyl-Sepharose-4B modified matrix (prepared as described in European Patent Application No. 83112555.4) previously equilibrated with 0.04 M borate buffer pH 7.5.

The column is washed with 8 l of water (acidified with 0.5 ml/l of 1 N hydrochloric acid). The column is then eluted with 1.5% (w/v) ammonia hydroxide collecting fractions of 100 ml each. Those fractions active against B. subtilis are pooled, concentrated under pressure and lyophilized to give 1.2 g of a desalted preparation of antibiotic A 42867 whose physico-chemical characteristics ar reported before.

We claim:

1. A biologically pure culture of Nocardia sp. ATCC 53492 or an antibiotic A 42867 producing mutant or varient thereof, said culture being capable of producing antibiotic A 42867 in a recoverable amount in an aqueous nutrient medium containing assimilable sources of carbon, nitrogen and inorganic substances.

2. The culture of claim 1 which iss Nocardia sp. ATCC 53492.

* * * * *